United States Patent [19]

Wolleb et al.

[11] Patent Number: 5,342,903
[45] Date of Patent: Aug. 30, 1994

[54] PROCESS FOR THE PREPARATION OF ADDUCTS OF EPOXIDES AND ALCOHOLS

[75] Inventors: Heinz Wolleb, Marly; Andreas Hafner, Laupen, both of Switzerland; William M. Rolfe, Balsham, England

[73] Assignee: Ciba-Geigy Corporation, Ardsley, N.Y.

[21] Appl. No.: 55,656

[22] Filed: Apr. 30, 1993

[30] Foreign Application Priority Data

May 6, 1992 [CH] Switzerland ............ 1455/92-1

[51] Int. Cl.$^5$ .............. C07C 41/03; C07D 301/28; C07D 303/04
[52] U.S. Cl. .............. 525/407; 525/523; 549/516; 568/607; 568/611; 568/618; 568/619; 568/620; 568/660; 568/662; 568/664; 568/670; 568/679; 568/680; 568/811; 568/822; 568/831; 568/867; 568/678; 568/866; 568/902
[58] Field of Search ............ 525/523, 407; 549/516; 568/664, 679, 607, 611, 618, 619, 620, 660, 662, 670, 678, 680

[56] References Cited

U.S. PATENT DOCUMENTS

| | | | |
|---|---|---|---|
| 2,538,072 | 6/1947 | Zech | 549/521 |
| 4,112,231 | 9/1978 | Weibull et al. | 544/174 |
| 4,543,430 | 9/1985 | Falgonx et al. | 568/678 |
| 4,707,535 | 11/1987 | Koleske | 528/110 |
| 4,957,946 | 9/1990 | Meier et al. | 528/92 |
| 5,162,547 | 11/1992 | Roth et al. | 549/516 |

FOREIGN PATENT DOCUMENTS

| | | |
|---|---|---|
| 0139042 | 5/1985 | European Pat. Off. |
| 2639564 | 3/1977 | Fed. Rep. of Germany |
| 2166738 | 5/1986 | United Kingdom |

*Primary Examiner*—Frederick Krass
*Attorney, Agent, or Firm*—William A. Teoli, Jr.

[57] ABSTRACT

A process for the preparation of adducts by reacting an alcohol with an epoxy compound in the presence of a catalyst, which comprises reacting an alcohol of formula I $$A{+}OH]_r \qquad (I)$$

wherein A is an aliphatic, cycloaliphatic or araliphatic radical and r is a number from 1 to 10, with a mono- or diepoxide in the equivalent ratio of 1:20 to 20:1, based on the hydroxyl and epoxy groups, in the presence of a metal complex of formula II as catalyst $$[M^{n+}(L_1)_x(L_2)_y(L_3{}^{m-})_z][X^{k-}]_{(n-zm)/k} \qquad (II),$$

wherein
M is a metal of the main groups or subgroups of the Periodic Table of the Elements,
$L_1$ and $L_2$ are weakly bonded, neutral, unidentale or multidentate ligands,
$L_3$ is a strongly bonded, non-replaceable neutral or anionic unidentale or multidentate ligand,
X is an anion of the following formulae $BF_4{}^-$, $PF_6{}^-$, $AsF_6{}^-$, $SbF_6{}^-$, $ClO_4{}^-$, $IO_4{}^-$, $NO_3{}^-$ or is the sulfonate radical of a perfluorinated alkanesulfonic acid,
n is an integer from 1 to 6,
m is 0 or an integer from 1 to 6,
k is 1 or 2,
x is an integer from 1 to 1000,
y is 0 or an integer from 1 to 1000, and
z is 0 or an integer from 1 to 6.

12 Claims, No Drawings

PROCESS FOR THE PREPARATION OF ADDUCTS OF EPOXIDES AND ALCOHOLS

The present invention relates to a process for the preparation of adducts by reacting aliphatic, cycloaliphatic or araliphatic alcohols with mono- or diepoxides in the presence of specific metal complexes as catalysts.

A process for the preparation of adducts of alkylene oxide or epichlorohydrin and hydroxylated compounds in the presence of tetraalkylammonium triflate or a specific metal salt of trifluoromethanesulfonic acid is disclosed in U.S. Pat. No. 4,543 430. By virtue of their preparation, these adducts belong to the aqua complexes which contain water of crystallisation.

The use of aqua complexes containing water of crystallisation of metal salts of specific sulfonic acids as catalysts for the advancement of epoxy resins with alcohols is disclosed in EP-A-0 139 042.

In GB patent 2 166 738 it is proposed to use metal perchlorates as catalysts for the preparation of adducts of epoxy compounds and alcohols.

The use of sodium fluoroborate and specific metal perchlorates, some of which are aqua complexes that contain water of crystallisation, is also proposed in DE-OS 26 35 564 for the preparation of adducts of epoxy compounds and alcohols.

It has now been found that the reaction of aliphatic, cycloaliphatic or araliphatic alcohols with mono- or diepoxides using catalyst systems based on metal complexes that wholly or partially contain ligands other than water proceeds much more selectively and, by comparison, in the preparation of glycidyl ethers results in the formation of glycidyl ethers having lower chlorine and higher epoxy values.

Accordingly, the invention relates to a process for the preparation of adducts by reacting an alcohol with an epoxy compound in the presence of a catalyst, which process comprises reacting an alcohol of formula I

$$A\text{\textendash}[OH]_r \quad (I)$$

wherein A is an aliphatic, cycloaliphatic or araliphatic radical and r is an integer from 1 to 10, with a mono- or diepoxide in the equivalent ratio of 1:20 to 20:1, based on the hydroxyl and epoxy groups, in the presence of a metal complex of formula II as catalyst

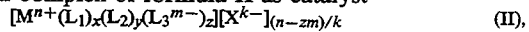

$$[M^{n+}(L_1)_x(L_2)_y(L_3^{m-})_z][X^{k-}]_{(n-zm)/k} \quad (II),$$

wherein

M is a metal of the main groups or subgroups of the Periodic Table of the Elements, $L_1$ and $L_2$ are weakly bonded, neutral, unidentate or multidentate ligands, $L_3$ is a strongly bonded, non-replaceable neutral or anionic unidentate or multidentate ligand, X is an anion of the following formulae $BF_4^-$, $PF_6^-$, $AsF_6^-$, $SbF_6^-$, $ClO_4^-$, $IO_4^-$, $NO_3^-$ or is the sulfonate radical of a perfluorinated alkanesulfonic acid, n is an integer from 1 to 6, m is 0 or an integer from 1 to 6, k is 1 or 2, x is an integer from 1 to 1000, y is 0 or an integer from 1 to 1000, and z is 0 or an integer from 1 to 6.

In formula I, an aliphatic radical A may be straight-chain or branched, saturated or unsaturated and be interrupted in the chain by one or more than one oxygen or sulfur atom or contain one or more than one keto group.

The cycloaliphatic radical A may be saturated or unsaturated and contain a keto group, and the rings may be substituted and/or bridged by alkyl groups.

The aromatic moiety of the araliphatic radical A may contain one or more than one ring or fused ring, typically phenyl, naphthyl, 4,4′-diphenyl, 4,4′-diphenylmethane, 4,4′-diphenyl(dimethyl)methane, 4,4′-diphenyloxide, 4,4′-diphenylketone or 4,4′-diphenylsulfone radicals which in turn may be substituted by $C_1$-$C_6$alkyl, $C_1$-$C_6$alkoxy or halogen. Araliphatic radicals are preferably aralkyl radicals in which alkyl may be unbranched or branched and preferably contains 1 to 3 carbon atoms.

$C_1$-$C_6$Alkyl and $C_1$-$C_6$alkoxy may be straight-chain or branched and are typically methyl, ethyl, propyl, isopropyl, butyl, sec-butyl, tert-butyl, pentyl and hexyl; and methoxy, ethoxy, propoxy, isopropoxy, butoxy, tert-butoxy, pentoxy and hexyloxy.

Halogen may be chloro, bromo or iodo, but is preferably bromo and, most preferably, chloro.

The radical A may be substituted by functional groups, provided they do not inhibit the catalyst and do not undergo side-reactions with the epichlorohydrin.

The radical A defined as alkyl group, when r=1, is typically $C_1$-$C_{30}$alkyl, preferably $C_3$-$C_{20}$alkyl. Representative examples of such radicals are methyl, ethyl, n-propyl, isopropyl, n-butyl, sec-butyl, tert-butyl, pentyl, hexyl, heptyl, octyl, 2-ethylhexyl, nonyl, decyl, dodecyl, tetradecyl, hexadecyl, octadecyl, icosyl, docosyl, tetracosyl and pentacosyl.

Cycloalkyl radicals are typically cyclopentyl, cyclohexyl, cycloheptyl, cyclooctyl and cyclononyl. Cyclohexyl is preferred.

Exemplary polyfunctional alcohols of formula I are those containing aliphatic, cycloaliphatic or araliphatic structural units, typically ethylene glycol, 1,2-propanediol, 1,3-propanediol, 1,4-butanediol, 1,2-butanediol, 2,3-butanediol, diethylene glycol, triethylene glycol, 1,5,-pentanediol, 1,6-hexanediol, 2,4,6-hexanetriol, 2,2-dimethyl-1,3-propanediol, 2-ethyl-2-butyl-1,2-propanediol, 1,12-dihydroxyoctadecane, glycerol, trimethylolpropane, erythritol, pentaerythritol, sorbitol, mannitol, inositol, 1,1,1-trimethylolpropane, 1,4-dimethylolbenzene, 4,4′-dimethyloldiphenyl, dimethylol xylenes, dimethylol naphthalenes, polyether alcohols such as diglycerol, also bis(2,3-dihydroxypropyl ether), triglycerol, dipentaerythritol, dimethylol anisoles, β-hydroxyethyl ethers of polyalcohols or phenols, such as diethylene glycol, polyethylene glycol or hydroquinonebis(β-hydroxyethyl ether), bis(β-hydroxyethyl ethers) of bisphenols, as of 4,4′-dihydroxydiphenyldimethylmethane, and also β-hydroxyethyl ethers of glycerol, pentaerythritol, sorbitol or mannitol, condensates of alkylene oxides, typically ethylene, propylene, butylene or isobutylene oxide, with the above mentioned polyalcohols, and hydroxy esters such as monoglycefides, e.g. monostearin, and ethylene glycol dilactate, monoesters of pentaerythritol, such as the monoacetate, and halogenated alcohols such as glycerol monochlorohydrin, 1,4-dichloro-2,3-dihydroxybutane, pentaerythritol monochlorides or dibromoneopentyl glycol, bis(4-hydroxycyclohexyl)methane, 2,2-bis(4-hydroxycyclohexyl)propane (perhydrobisphenol A), cyclohexane-1,1-dimethylol, 2,2,6,6-tetramethylolcyclohexanol, 2,2,5,5-tetramethylolcyclopentanol, 4- methyl-2,2,6,6-tetramethylolcyclohexanol, 2,2,6,6-tetramethylolcyclohexan-4-one, 1,2-, 1,3- and 1,4-dihydroxycyclohexane, 1,3-dihydroxycyclopentane, 4,4'-dihydroxydicyclohexyl, and mercaptoalcohols such as 2-mercaptoethanol, α-monothioglycerol, 2,2',3,3'-tetrahydroxydipropylsulfide or 2,2'-dihydroxydiethylsulfide.

Preferably A in formula I is an aliphatic or cycloaliphatic radical, most preferably an aliphatic radical.

In formula I, r is preferably an integer from 1 to 6.

Especially preferred compounds of formula I in the practice of this invention are primary or secondary polyfunctional alcohols in which r is an integer from 2 to 6, and most preferably A is a polyfunctional radical of up to 30 carbon atoms, in which case r is an integer from 1 to 6.

Monoepoxides useful in the practice of this invention are all customary monoepoxides, but it is preferred to use an epihalohydrin, typically epichlorohydrin, β-methylepichlorohydrin or epibromohydrin and, most preferably, epichlorohydrin, or an alkylene oxide such as ethylene oxide, 1,2-propylene oxide or 1,2-butylene oxide.

Diepoxides useful in the practice of this invention are likewise all customary diepoxides. Typical examples are the diglycidyl ethers of the aforementioned diols or the diglycidyl ethers of diphenols, for example resorcinol, hydroquinone or 4,4'-dihydroxybiphenyl, preferably of bisphenols such as bis(4-hydroxyphenyl)methane, bis(4-hydroxyphenyl)sulfone, 2,2'-bis(4-hydroxyphenyl)propane as well as the diglycidyl esters of aliphatic dicarboxylic acids, for example oxalic acid, succinic acid, glutaric acid, or adipic acid, of cycloaliphatic dicarboxylic acids such as tetrahydrophthalic acid, 4-methyltetrahydrophthalic acid or hexahydrophthalic acid or of aromatic dicarboxylic acids such as phthalic acid, isophthalic acid or terephthalic acid. In the process of this invention it is also possible to use cycloaliphatic epoxy resins, for example bis(2,3-epoxycyclopentyl) ether, 2,3-epoxycyclopentyl glycidyl ether, 1,2-bis(2,3-epoxycyclopentyloxy)ethane or 3,4-epoxycyclohexylmethyl-3,4'-epoxycyclohexanecarboxylate.

In the process of this invention it is preferred to use a monoepoxide, typically an epihalohydrin or an alkylene oxide, most preferably an epihalohydrin.

The addition of an epihalohydrin to the alcohol of formula I results in the formation of a halohydrin ether which is conveniently not isolated but is dehydrohalogenated with a base direct to give the glycidyl ether of formula III

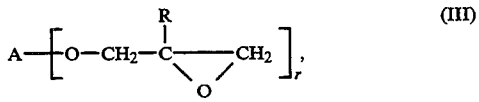

(III)

wherein A and r are as defined for formula I and R is a hydrogen atom or methyl.

Accordingly, the invention also relates to a process for the preparation of compounds of formula III, which comprises subsequently dehydrohalogenating the halohydrin ethers obtained as intermediates by addition of epihalohydrin to the alcohols of formula I with a base to give the glycidyl ethers of formula III.

The ephihalohydrin used for the addition to the alcohols of formula I is preferably epichlorohydrin.

The epihalohydrin is conveniently used in an amount such as to provide from 0.7 to 2.0 mol of epihalohydrin per equivalent of hydroxyl group of the compound of formula I. Stoichiometric amounts, however, are preferred, i.e. 0.9 to 1.1 mol of epihalohydrin per equivalent of hydroxyl group.

The metal catalysts of formula II used in the process of this invention are known, e.g. from Gmelin, Vol. 39, Part C5, page 39 et seq., or Inorganic Chemistry, 21, page 2867 et seq. (1982), and can be conveniently prepared by reacting a metal oxide or a metal salt, for example a metal halide or metal carbonate, with the acid forming the anion X, in the presence of a compound that forms the ligand $L_1$ and/or the ligand $L_2$ and/or $L_3$.

Suitable compounds that form the ligand $L_1$ are typically nitriles, isonitriles, thioethers, phosphines, ethers, aldehydes, ketones or $sp^3$-nitrogen-containing compounds; and suitable compounds that form the ligand $L_2$ are typically water, nitriles, isonitriles, thioethera, phosphines, ethers, aldehydes, ketones or $sp^3$-nitrogen-containing compounds.

Suitable compounds that form the ligand $L_3$ are typically phosphines, phosphites, phosponites, halides, cyanides, alcoholates, thiolates, carboxylates, acetylacetonate, a cyclopentadienyl, unsubstituted or substituted by one or more than one $C_1$–$C_4$alkyl group, or $sp^2$-nitrogen-containing compounds.

Suitable nitriles that form the ligands $L_1$ and $L_2$ are typically aliphatic, araliphatic oder aromatic nitriles, for example acetonitrile, propionitrile, n-butyronitrile, isobutyronitrile, valeronitrile, tetradecanonitrile, malononitril, succinonitrile, glutaronitrile, acrylonitrile, methacrylonitrile, allyl cyanide, phenylacetonitrile, benzoyl cyanide, benzonitrile, 2-chloro-, 4-chloro- or 2,6-dichlorobenzonitrile, 2-chloro-4-nitrobenzonitrile, 4-hydroxybenzonitrile or 1-cyanonaphthalene.

Suitable isonitriles that form the ligands $L_1$ and $L_2$ are likewise aliphatic, araliphatic oder aromatic isonitriles, for example methyl isocyanide, n-butyl isocyanide, phenyl isocyanide or 3-chlorophenyl isocyanide.

Suitable thioethers (organic sulfides) that form the ligands $L_1$ and $L_2$ are typically aliphatic, araliphatic oder aromatic thioethers, for example diethyl sulfide, dipropyl sulfide, ethylphenyl sulfide, diphenyl sulfide, benzylphenyl sulfide, dibenzyl sulfide or 4-(ethylthio)-phenol.

Suitable phosphines that form the ligands $L_1$ and $L_2$ are typically aliphatic, araliphatic oder aromatic phosphines. These may be primary, secondary or tertiary phosphines, depending on whether 1,2 or 3 hydrogen atoms of the hydrogen phosphide $PH_3$ are substituted by organic groups. Exemplary phosphines are trimethylphosphine, triethylphosphine, tribenzylphosphine or triphenylphosphine.

Suitable ethers that form the ligands $L_1$ and $L_2$ may typically be aliphatic, araliphatic, cycloaliphatic or aromatic ethers, such as dimethyl ether, diethyl ether, di-n-propyl ether, diisopropyl ether, di-n-butyl ether, bis(chloromethyl) ether, bis(chloroethyl) ether, methyl-n-propyl ether, methyl tert-butyl ether, vinyl ether, e.g. methyl or ethyl vinyl ether, allyl ethers such as allyl phenyl ether; benzyl phenyl ether, furan, tetrahydrofuran, dioxane, crown ethers such as 18-crown-6, 15-crown-5 or 12-crown-4; phenyl methyl ether, phenyl ethyl ether or diphenyl ether.

Suitable aldehydes that form the ligands $L_1$ and $L_2$ may typically be aliphatic, araliphatic or aromatic ethers, such as formaldehyde (methanal), acetaldehyde (ethanal), butyraldehyde (butanal), 2-methylbutanal, 2,2-dimethylpropanal, 2-ethylhexanal; 2,2-dimethylpentanal, 2-hydroxyethanal, 2-phenylacetaldehyde, 2-phenylpropanal, 3-phenyl-2-propanal (cinnamaldehyde), benzaldehyde or anisaldehyde.

A ketone as the ligands $L_1$ and $L_2$ is an aliphatic, araliphatic, cycloaliphatic or aromatic compound containing preferably one or two keto groups in the molecule, such as acetone, methyl ethyl ketone, ethyl propyl ketone, diisopropyl ketone, acetophenone, propiophenone, chalcone, desoxybenzoin, 2,4-hexanedione, 1,4-benzoquinone, cyclopentanone, cyclohexanone, 1,4-naphthoquinone, anthraquinone or benzophenone.

Possible ligands $L_1$ and $L_2$ are also those that contain a plurality of different ligand positions in a molecule, for example methoxyacetaldehyde, 2-methoxyacetophenone or 2-methoxybenzaldehyde.

A $sp^3$-nitrogen-containing compound as the ligands $L_1$ and $L_2$ is a tertiary nitrogen compound that does not contain double bonds and is typically trimethylamine, triethylamine, tributylamine, triisobutylamine, tripentylamine or triphenylamine.

The compounds cited as suitable ligands $L_1$ and $L_2$ are known and most are commercially available.

Suitable compounds that form the ligand $L_3$ are typically phosphines, phosphites, phosphonites, halides, cyanides, alcoholates, thiolates, carboxylates, acetylacetonates, cyclopentadienyls or $sp^2$-nitrogen-containing compounds which are unsubstituted or substituted by one or more than one $C_1$–$C_4$alkyl or tri($C_1$–$C_4$alkyl)silyl group.

Suitable phosphines that form the ligand $L_3$ are typically the aliphatic, araliphatic or aromatic phosphines cited in connection with the ligands $L_1$ and $L_2$.

A phosphite that forms the ligand $L_3$ is an anion of phosphorous acid $P(OH)_3$ or an ester of phosphorous acid, typically dimethyl phosphite, diethyl phosphite, trimethyl phosphite or triethylphosphite.

A phosphonite that forms the ligand $L_3$ is an anion or ester of phosphonous acid $HP(OH)_2$, preferably of organically substituted phosphonous acid, e.g. methyl-, octyl- or phenylphosphonous acid.

A halide that forms the ligand $L_3$ is $F^-$, $Cl^-$, $Br^-$ or $I^-$.

A cyanide that forms the ligand $L_3$ is the cyanide anion.

A thiolate (mercaptide) that forms the ligand $L_3$ is an anion of thiols R-SH, wherein R is an alkyl or aryl group.

A carboxylate that forms the ligand $L_3$ is an anion of saturated or unsaturated aliphatic monocarboxylic acids, typically acetic acid, propionic acid, butyric acid, caproic acid, lauric acid, palmitic acid, acrylic acid, methacrylic acid, propiolic acid, crotonic acid, sorbic acid or oleic acid; of cycloaliphatic monocarboxylic acids such as cycylohexanecarboxylic acid; of aromatic carboxylic acids such as benzoic acid, naphthoic acids or tolyl acids; or of araliphatic monocarboxylic acids such as hydrotropaic acid, atropaic acid or cinnamic acids.

A $sp^2$-nitrogen-containing compound that forms the ligand $L_3$ is a compound containing the —N≡C bond, e.g. an azomethine such as benzalaniline or benzalimine.

Metal catalysts useful in the process of this invention are preferably those wherein in formula III
  A is a metal of main group II, III or IV of the Periodic Table of the Elements, a metal of the transition groups, a lanthanide or actinide,
  $L_1$ is a nitrile, isonitrile, thioether, phosphine, ether, aldehyde, ketone or a $sp^2$-nitrogen-containing compound,
  $L_2$ is a water molecule, a nitrile, isonitrile, thioether, phosphine, ether, aldehyde, ketone or a $sp^2$-nitrogen-containing compound,
  $L_3$ is a phosphine, phosphite, phosponite, halide, cyanide, alcoholate, thiolate, carboxylate, acetylacetonate, a cyclopentadienyl or $sp^2$-nitrogen-containing compound which is unsubstituted or substituted by one or more than one $C_1$–$C_4$alkyl or tri($C_1$–$C_4$alkyl)silyl group,
  X is an anion of the following formulae $BF_4^-$, $PF_6^-$, $AsF_6^-$, $SbF_6^-$, $ClO_4^-$, $IO_4^-$, $NO_3^-$ or is the sulfonate radical of a perfluorinated alkanesulfonic acid,
  n is an integer from 1 to 3,
  m is 0 or an integer from 1 to 3,
  k is 1 or 2,
  x is an integer from 1 to 10,
  y is 0 or an integer from 1 to 10, and
  z is 0 or an integer from 1 to 3.

X as a sulfonate radical, i.e. an anion of a perfluorinated alkanesulfonic acid, may typically be one of the following anions: $CF_3SO_3^-$, $C_8F_{17}SO_3^-$, $CF_3C_6F_{10}SO_3^-$, $C_3F_7SO_3^-$, $C_2F_5SO_3^-$, $C_2HF_4SO_3^-$, $C_3F_7CHFCF_2SO_3^-$, $(CF_3)_2CHCF_2SO_3^-$, $C_4F_7SO_3^-$, $(CF_3)_2CF(CF_2)_4SO_3^-$, $C_4F_9CFHCF_2SO_3^-$, $C_3F_7CH(CF_3)CF_2SO_3^-$, $C_{11}F_{23}SO_3^-$, $C_5H_{11}CFHCF_2SO_3^-$ or $C_7F_{15}CFHCF_2SO_3^-$. Preferably X is $CF_3SO_3^-$.

It is especially preferred to use in the process of this invention a metal catalyst of formula II, wherein
  A is Fe, Sn, Zn, Y or a metal of the lanthanides,
  $L_1$ is a nitrile, isonitrile, thioether or ether,
  $L_2$ is a water molecule, a nitrile, isonitrile, thioether or ether,
  $L_3$ is a phosphine, phosphite, halide or carboxylate,
  X is an anion of the following formulae $BF_4^-$, $PF_6^-$, $ClO_4^-$ or is the trifluoromethanesulfonate radical.

Especially suitable catalysts of formula II for the process of this invention are $La(CH_3CN)_x(H_2O)_y(CF_3SO_3)_3$ and $La(CH_3CN)_x(H_2O)_y(ClO_4)_3$.

Without adversely affecting the reaction, the metal catalysts of formula II can be used in a wide range of concentration; but a concentration of 0.001 to 0.5 mol of catalyst to 1 mol of alcohol of formula I is advantageous.

The catalyst can either be prepared separately or in situ.

The reaction of the compounds of formula I with the mono- and diepoxides is conveniently carded out without a solvent, but can also be carded out in the presence of an inert organic solvent. Suitable solvents are typically halogenated hydrocarbons such as methylene chloride, chloroform, 1,2-dichloroethane, 1,1,1-trichloroethane, 1,2,2-trichloroethylene, 1,4-dichloropropane and chlorobenzene, also toluene, xylene, hexane, cyclohexane, heptane, octane, and esters such as ethyl acetate and butyl acetate, ethers such as diethyl and diisopropyl ether, dioxane and tetrahydrofuran. Mixtures of the above solvents in all ratios can also be used.

The amount of solvent or mixture of solvents can vary freely, but is conveniently chosen such that the concentration of reactants is in the range from 10 to 70% by weight.

The reaction of the alcohol with the mono- or diepoxide is conveniently carded out in the temperature range from 0° C. to the reflux temperature of the reaction mixture, preferably from 60° to 130° C. The total reaction times vary, depending on the alcohol and catalyst, from 30 minutes to 48 hours. The reaction may in some cases be carded out under increased or reduced pressure.

The order in which the components are added when carrying out the novel process is not important. Thus, for example, it is possible to charge the alcohol and the catalyst to the reactor and then to add the epoxy compound, or all the reaction components are charged to the reactor and reacted together. The reaction is carded out until analysis of the reaction mixture indicates the desired conversion.

Possible variants of the process are the preferred embodiment of the process, namely the reaction of the alcohol of formula I with epichlorohydrin. The alcohol and the catalyst are charged together to the reactor and heated to the required reaction temperature. The epihalohydrin is then added over suitable periods of time such that the temperature remains within a suitable range. The reaction is thereafter allowed to continue until analysis of the reaction mixture (e.g. by gas chromatographgy, epoxide titration or HPLC) indicates the desired conversion to the corresponding halohydrin ether. All components, i.e. the alcohol, the epihalohydrin and the catalyst, are charged to the reactor and heated to the required reaction temperature, and further reacted until the desired conversion of epihalohydrin ether. Any excess of epihalohydrin can be removed from the reaction mixture by distillation prior to dehydrohalogenation.

The dehydrohalogenation of the halohydrin ether to the glycidyl ether can be carried out by the known standard methods with an alkali metal hydroxide as base with elimination of alkali metal halide. The theoretical requisite stoichiometric amount may also on occasion be exceeded or be less in order to achieve the optimum low chlorine values of the final product. Ordinarily amounts of 0.80 to 1.3 mol of alkali metal hydroxide per hydroxyl group and temperatures ranging from 30° to 60° C. are preferred. The use of an inert organic solvent is indicated whenever the viscosity of the reaction mixture is too high.

In some cases the glycidylation may conveniently be carded out by removing the water as an azeotrope in the presence of alkali metal hydroxide. It is preferred to add the alkali metal hydroxide during the azeotropic removal of water under reduced pressure. Water that acts as solvent for the alkali metal hydroxide and water that is formed during the reaction is thus continuously removed from the reaction mixture.

The salt formed during the reaction, e.g. sodium chloride, can either be washed out or removed by filtration or centrifugation. Excess epihalohydrin may be removed by vacuum distillation.

The starting compounds for the process of this invention are known products and some are commercially available.

The improved process of this invention has a number of advantages over the known processes of the prior art, including enhanced selectivity resulting in lower chlorine and higher epoxy values.

In addition, the first reaction step can often be carded out in the melt without a solvent.

The compounds obtained by the process of this invention are frequently used in epoxy resin formulations for modifying specific properties, typically as reactive diluents, flexibilisers or adhesion improvers. These formulations may contain other additional epoxy resins, conveniently bisphenol A epoxy resins or epoxy novolaks, and customary hardeners such as amines, carboxylic anhydrides, phenols or catalytic hardeners. The formulations find utility in many different fields of application, for example as film-forming resins, primers, impregnating resins, adhesives, sealants, coating compositions and insulating materials. Owing to their aliphatic structure, the novel glycidyl ethers have excellent resistance to weathering.

The invention is illustrated in more detail by the following examples in which, unless otherwise indicated, pans are by weight.

The following metal complexes, which can be prepared as follows, are used in the Examples.

Catalyst A: $La(CH_3CN)_x(H_2O)_y(CF_3SO_3)_3$

A three-necked flask equipped with magnetic stirrer, $N_2$ inlet and septum is charged with 3.0 g (5 mmol) of $La_2(CO_3)_3(H_2O)_y$ in 50 ml of acetonitrile dried over a molecular sieve and then 4 ml (46 mmol) of trifluoromethanesulfonic acid are added. The suspension is stirred for 24 hours (h) at room temperature (RT) to form a white paste. The reaction mixture is filtered through a glass frit and washed with 4×50 ml of diethyl ether freshly distilled over sodium. The residue is dried for 24 h at $RT/10^{-2}T$, giving 5 g of a white solid for which the following analytical data are obtained:

La content = 24.9%
C content = 9.34%
N content = 1.91%.

Catalyst B: $La(H_2O)_y(CF_3SO_3)_3$ with benzyl phenyl sulfide as ligand $L_1$ 10 ml of water are placed into a three-necked flask equipped with magnetic stirrer and 3.45 g (23 mmol) of trifluoromethanesulfonic acid are added. Then 3.0 g (5 mmol) of $La_2(CO_3)_3(H_2O)_y$ are added and the solution is stirred until neutral. The solution is then filtered and the filtrate is concentrated to dryness on a rotary evaporator at 100° C., giving 5.6 g of $La(H_2O)_y(CF_3SO_3)_3$ as a white solid which has a La content of 24.5%. 1.38 g of the solid are suspended in 200 ml of toluene and, by adding 0.6 g (3 mmol) of benzyl phenyl sulfide at 100° C., catalyst B which is used direct in Example 2 is obtained.

Catalyst C: $La(CH_3CN)_x(H_2O)_y(ClO_4)_3$ 8 ml of water and 788 mg (5.5 mmol) of 70% aqueous perchloric acid are charged to a three-necked flask equipped with magnetic stirrer. Then 1 g of $La_2(CO_3)_3(H_2O)_y$ is added and the suspension is stirred until neutral. Afterwards the suspension is filtered and the filtrate is transferred to a 750 ml sulfonation flask equipped with anchor stirrer, thermometer, metering device and distillation head. The aqueous phase is covered with a 300 ml layer of toluene and the mixture is heated at an oil bath temperature of 140° C. As soon as the still temperature of the distillate is 105° C., 100 ml of acetonitrile dried over a molecular sieve are added and excess acetonitrile is removed by distillation. As soon as the still temperature is again 105° C., the procedure is repeated with 50 ml of acetonitrile. This catalyst solution is used direct in Example 3.

Catalyst D: $La(H_2O)_y(ClO_4)_3$ with benzyl phenyl sulfide as ligand $L_1$ 8 ml of water and 788 mg (5.5 mmol) of 70% aqueous perchloric acid are charged to a three-necked flask equipped with magnetic stirrer. Then 1 g of $La_2$(-

$CO_3)_3(H_2O)_x$ is added and the suspension is stirred until neutral. Afterwards the suspension is filtered and the filtrate is transferred to a 750 ml sulfonation flask equipped with anchor stirrer, thermometer, metering device and distillation head. The aqueous phase is covered with a 300 ml layer of toluene and the mixture is heated at an oil bath temperature of 140° C. As soon as the still temperature of the distillate is 105° C., the distillation head is replaced with a reflux condenser and 551 mg (2.75 mmol) of benzyl phenyl sulfide are added. This catalyst solution is used direct in Example 4.

Catalyst E: $Cu(CH_3CN)_x(H_2O)_yCF_3SO_3$

A three-necked flask equipped with magnetic stirrer, $N_2$ inlet and septum is charged with 2.15 g (15 mmol) of $Cu_2O$ in 50 ml of acetonitrile dried over a molecular sieve and then 5.06 ml (34 mmol) of trifluoromethanesulfonic acid (triflate) are added. The red suspension dissolves at once to form a clear, yellowish solution which is added dropwise to 150 ml of diethyl ether freshly distilled over sodium. The resultant white precipitate is collected by filtration and washed with $4 \times 50$ ml of diethyl ether. The product is dried for 2 h at RT/0.013 mbar, giving 8.41 g of a white powder having a Cu content of 16.8%.

Catalyst F: $Zn(H_2O)_y(CF_3SO_3)_2$ with benzyl phenyl sulfide as ligand $L_1$

A three-necked flask equipped with magnetic stirrer is charged with 30 ml of $H_2O$ and 4.20 g (28 mmol) of trifluoromethanesulfonic acid and 1.22 g (15 mol) of ZnO are added. As soon as the solution shows neutral reaction, the reaction mixture is filtered and the filtrate is freed from solvent at 100° C. on a rotary evaporator, giving 5.1 g of a white powder which has a Zn content of 17.8%. 0.94 g of the white powder is dissolved in 90.12 g (1.0 mol) of 1,4-butanediol, then 0.6 g (3 mmol) of benzyl phenyl sulfide are added. This catalyst is used direct in Example 6.

Catalyst G: $Zn(CH_3CN)_x(H_2O)_y(BF_4)_2$

A three-necked flask equipped with magnetic stirrer, $N_2$ inlet and septum is charged with 1.63 g (20 mmol) of ZnO in 50 ml of acetonitrile dried over a molecular sieve and then 7.9 ml (55 mmol) of $HBF_4$.diethyl ether (54%) are added. The suspension dissolves at once to form a clear, yellowish solution which is added dropwise to 300 ml of diethyl ether freshly distilled over sodium. The resultant white precipitate is isolated by filtration and washed with $4 \times 50$ ml of diethyl ether. The product is dried for 2 h at RT/0.013 mbar, giving 5.6 g of a white powder for which the following analytical data are obtained:

Zn content = 17.30%
C content = 16.25%
N content = 9.18%.

Catalyst H: $Fe(CH_3CN)_x(H_2O)_y(CF_3SO_3)_2$

To a solution of 15.5 g (0.0356 mol) of barium triflate in 50 ml of water are added 9.9 g (0.0356 mol) of $FeSO_4.7H_2O$ in 50 ml of water. The precipitate consisting of $BaSO_4$ is removed by filtration and the filtrate is freed from solvent at 100° C. on a rotary evaporator, giving 11.8 g of $Fe(H_2O)_y(CF_3SO_3)_2$.2.5 g of $Fe(H_2O)_y(CF_3SO_3)_2$ are dissolved in 10 ml of acetonitrile and the solution is filtered. To the filtrate are added 30 ml of diethyl ether and the solvent is then removed by distillation on a rotary evaporyator. The residue is then dried at 100° C. under vacuum, giving a white solid for which the following analytical data are obtained:

C content = 14.57%
N content = 4.97%
H content = 2.06%.

EXAMPLE 1

A 750 ml sulfonation flask equipped with thermometer, reflux condenser, $N_2$ inlet and metering device, is charged with 90.12 g (1.0 mol) of 1,4-butanediol and 1.66 g of catalyst A and the reaction mixture is heated to 100° C. With efficient stirring, 160.7 ml (2.05 mol) of epichlorohydrin are added over 1 h and the mixture is allowed to react for 1 h. Afterwards the reaction mixture is cooled to 50° C., 200 ml of toluene are added and to the solution are added 16 g (0.2 mol) of a 50% aqueous solution of NaOH over 5 minutes (min). Then 76 g (1.9 mol) of pulverised NaOH are added by increments over 5 min and the suspension is stirred for 30 min. The reaction mixture is filtered, washed with 100 ml of toluene and the phases are separated. The organic phase is dried over $MgSO_4$, filtered and the filtrate is freed from solvent on a rotary evaporator (bath temperature 70° C.), giving 204.8 g (101% of theory) of colourless diglycidyl ether of 1,4-butanediol having the following properties: epoxy value: 8.59 eq/kg (87% of theory); total chlorine content: 3.8%; concentration of hydrolisable chlorine: 29 ppm (parts per million).

EXAMPLE 2

In a 750 ml sulfonation flask equipped with thermometer, reflux condenser, $N_2$ inlet and metering device, 90.12 g (1.0 mol) of 1,4-butanediol are added to catalyst B and the reaction mixture is heated to 100° C. With efficient stirring, 160.7 ml (2.05 mol) of epichlorohydrin are added over 1 h and the mixture is allowed to react for 1 h. Afterwards the reaction mixture is cooled to 50° C. and to the solution are added 16 g (0.2 mol) of a 50% aqueous solution of NaOH over 5 min. Then 76 g (1.9 mol) of pulverised NaOH are added by increments over 45 min and the suspension is stirred for 30 min. The reaction mixture is filtered, washed with 100 ml of toluene and the phases are separated. The organic phase is dried over $MgSO_4$, filtered and the filtrate is freed from solvent on a rotary evaporator (bath temperature 70° C.), giving 199.0 g (98% of theory) of colourless diglycidyl ether of 1,4-butanediol having the following properties: epoxy value: 8.64 eq/kg (87% of theory); total chlorine content: 3.4%; concentration of hydrolisable chlorine: 620 ppm.

EXAMPLE 3

The solution of catalyst C is further used in the apparatus in which the distillation head is replaced with a reflux condenser. To the catalyst solution are added 90.12 g (1.0 mol) of 1,4-butanediol and then 160.7 ml (2.05 mol) of epichlorohydrin are added under $N_2$ and with good stirring over 1 h. The reaction mixture is thereafter allowed to react for 3 h under reflux, then cooled to 50° C. To the solution are then added 16 g (0.2 mol) of a 50% aqueous solution of NaOH over 5 min, followed by the addition of 76 g (1.9 mol) of pulverised NaOH in increments over 45 min. The suspension is stirred for 30 minutes. The reaction mixture is filtered, washed with 100 mol of toluene and the phases are separated. The organic phase is dried over $MgSO_4$, filtered, and the filtrate is freed from solvent on a rotary evaporator at a bath temperature of 70° C., giving 203.0 g (100% of theory) of colourless diglycidyl ether of 1,4-butanediol having the following properties: epoxy value: 8.78 eq/kg (89% of theory); total chlorine content: 3.6%; concentration of hydrolisable chlorine: 50 ppm.

EXAMPLE 4

The solution of catalyst D is further used in the apparatus used for carrying out the reaction. To the catalyst solution are added 90.12 g (1.0 mol) of 1,4-butanediol and then 160.7 ml (2.05 mol) of epichlorohydrin are added under $N_2$ and with good stirring over 1 h. The reaction mixture is thereafter allowed to react for 3 h under reflux, then cooled to 50° C. To the solution are then added 16 g (0.2 mol) of a 50% aqueous solution of NaOH over 5 min, followed by the addition of 76 g (1.9 mol) of pulverised NaOH in increments over 45 min. The suspension is stirred for 30 minutes. The reaction mixture is filtered, washed with 100 mol of toluene and the phases are separated. The organic phase is dried over $MgSO_4$, filtered, and the filtrate is freed from solvent on a rotary evaporator at a bath temperature of 70° C., giving 205.0 g (101% of theory) of colourless diglycidyl ether of 1,4-butanediol having the following properties: epoxy value: 8.68 eq/kg (88% of theory); total chlorine content: 3.2%; concentration of hydrolisable chlorine: 110 ppm.

EXAMPLE 5

A 750 ml sulfonation flask equipped with thermometer, reflux condenser, $N_2$ inlet and metering device is charged with 90.12 g (1.0 mol) of 1,4-butanediol and 0.75 g of catalyst E and the reaction mixture is heated to 100° C. With efficient stirring, 164.7 ml (2.10 mol) of epichlorohydrin are added, and the reaction mixture is thereafter allowed to react for 5 h. After cooling to 50° C., 200 ml of toluene are added and to the solution are then added 16 g (0.2 mol) of a 50% aqueous solution of NaOH over 5 min, followed by the addition of 76 g (1.9 mol) of pulverised NaOH in increments over 45 min. The suspension is stirred for 30 minutes. The reaction mixture is filtered, washed with 100 mol of toluene and the phases are separated. The organic phase is dried over $MgSO_4$, filtered, and the filtrate is freed from solvent on a rotary evaporator at a bath temperature of 70° C., giving 205.4 g (101% of theory) of yellowish diglycidyl ether of 1,4-butanediol having the following properties: epoxy value: 7.61 eq/kg (77% of theory); total chlorine content: 6.2%; concentration of hydrolisable chlorine: 230 ppm.

EXAMPLE 6

In a 750 ml sulfonation flask equipped with thermometer, reflux condenser, $N_2$ inlet and metering device, a solution of catalyst F is added to 1,4-butanediol and the reaction mixture is heated to 100° C. With efficient stirring, 164.7 ml (2.10 mol) of epichlorohydrin are added, and the reaction mixture is thereafter allowed to react for 7 h. After cooling to 50° C., 200 ml of toluene are added and to the solution are then added 16 g (0.2 mol) of a 50% aqueous solution of NaOH over 5 min, followed by the addition of 76 g (1.9 mol) of pulverised NaOH in increments over 45 min. The suspension is stirred for 30 minutes. The reaction mixture is filtered, washed with 100 mol of toluene and the phases are separated. The organic phase is dried over $MgSO_4$, filtered, and the filtrate is freed from solvent on a rotary evaporator at a bath temperature of 70° C., giving 196.0 g (97% of theory) of yellowish diglycidyl ether of 1,4-butanediol having the following properties: epoxy value: 8.22 eq/kg (83% of theory); total chlorine content: 5.0%; concentration of hydrolisable chlorine: 170 ppm.

EXAMPLE 7

A 750 ml sulfonation flask equipped with thermometer, reflux condenser, $N_2$ inlet and metering device is charged with 90.12 g (1.0 mol) of 1,4-butanediol and 0.4 g of catalyst G and the reaction mixture is heated to 100° C. With efficient stirring, 172.43 ml (2.20 mol) of epichlorohydrin are added, and the reaction mixture is thereafter allowed to react for 1 h. After cooling to 50° C., 200 ml of toluene are added and to the solution are then added 16 g (0.2 mol) of a 50% aqueous solution of NaOH over 5 min, followed by the addition of 80 g (2.0 mol) of pulverised NaOH in increments over 45 min. The suspension is stirred for 30 minutes. The reaction mixture is filtered, washed with 100 mol of toluene and the phases are separated. The organic phase is dried over $MgSO_4$, filtered, and the filtrate is freed from solvent on a rotary evaporator at a bath temperature of 70° C., giving 220.2 g (109% of theory) of yellowish diglycidyl ether of 1,4-butanediol having the following properties: epoxy value: 7.64 eq/kg (77% of theory); total chlorine content: 7.5%; concentration of hydrolisable chlorine: 1500 ppm.

EXAMPLE 8

A 750 ml sulfonation flask equipped with thermometer, reflux condenser, $N_2$ inlet and metering device is charged with 114.19 g (1.0 mol) of 4-methylcyclohexanol and 1.7 g of catalyst A and the reaction mixture is heated to 100° C. With efficient stirring, 98.0 ml (1.25 mol) of epichlorohydrin are added, and the reaction mixture is thereafter allowed to react for 4 h. After cooling to 50° C., 1 g of tetramethylammonium chloride is added and to the solution are then added 8 g (0.1 mol) of a 50% aqueous solution of NaOH over 5 min, followed by the addition of 42 g (1.05 mol) of pulverised NaOH in increments over 45 min and the suspension is stirred for 5 h. After addition of 200 ml of ethyl acetate, the reaction mixture is filtered, washed with 100 ml of ethyl acetate and the phases are separated. The organic phase is dried over $MgSO_4$, filtered, and the filtrate is freed from solvent on a rotary evaporator at a bath temperature of 60° C., giving 170.7 g (100% of theory) of colourless glycidyl ether of 4-methylcyclohexanol having the following properties: epoxy value: 5.00 eq/kg (85% of theory); total chlorine content: 5.0%; concentration of hydrolisable chlorine: 3000 ppm.

EXAMPLE 9

In a 750 ml sulfonation flask equipped with thermometer, reflux condenser, $N_2$ inlet and metering device, 114.19 g (1.0 mol) of 4-methylcyclohexanol are added to 1.7 g of catalyst B and the reaction mixture is heated to 100° C. With efficient stirring, 98.0 ml (1.25 mol) of epichlorohydrin are added, and the reaction mixture is thereafter allowed to react for 3 h. After cooling to 50° C., 1 g of tetramethylammonium chloride is added and to the solution are then added 8 g (0.1 mol) of a 50% aqueous solution of NaOH over 5 min, followed by the addition of 42 g (1.05 mol) of pulverised NaOH in increments over 45 min and the suspension is stirred for 7 h. After addition of 200 ml of ethyl acetate, the reaction mixture is filtered, washed with 100 ml of ethyl acetate and the phases are separated. The organic phase is dried over $MgSO_4$, filtered, and the filtrate is freed from solvent on a rotary evaporator at a bath temperature of 60° C., giving 168.5 g (99% of theory) of colourless glycidyl ether of 4-methylcyclohexanol having the following properties: epoxy value: 4.93 eq/kg (84% of theory); total chlorine content: 4.75%; concentration of hydrolisable chlorine: 5900 ppm.

EXAMPLE 10

A 750 ml sulfonation flask equipped with thermometer, reflux condenser, $N_2$ inlet and metering device is charged with 114.19 g (1.0 mol) of 4-methylcyclohexanol and 0.81 g of catalyst G and the reaction mixture is heated to 100° C. With efficient stirring, 98.0 ml (1.25 mol) of epichlorohydrin are added, and the reaction mixture is thereafter allowed to react for 1 h. After cooling to 50° C., 1 g of tetramethylammonium chloride is added and to the solution are then added 8 g (0.1 mol) of a 50% aqueous solution of NaOH over 5 min, followed by the addition of 42 g (1.05 mol) of pulverised NaOH in increments over 45 min and the suspension is stirred for 5 h. After addition of 200 ml of ethyl acetate, the reaction mixture is filtered, washed with 100 ml of ethyl acetate and the phases are separated. The organic phase is dried over $MgSO_4$, filtered, and the filtrate is freed from solvent on a rotary evaporator at a bath temperature of 60° C., giving 184.2 g (108% of theory) of colourless glycidyl ether of 4-methylcyclohexanol having the following properties: epoxy value: 4.65 eq/kg (79% of theory); total chlorine content: 5.95%; concentration of hydrolisable chlorine: 330 ppm.

EXAMPLE 11

A 750 ml sulfonation flask equipped with thermometer, reflux condenser, $N_2$ inlet and metering device is charged with 78.14 g (0.5 mol) of 4-tert-butylcyclohexanol and 0.83 g of catalyst A and the reaction mixture is heated to 100° C., whereupon the educt melts. With efficient stirring, 39.2 ml (0.5 mol) of epichlorohydrin are added, and the reaction mixture is thereafter allowed to react for 6 h. After cooling to 50° C., 2 g of tetramethylammonium chloride are added and to the solution are then added 4 g (0.05 mol) of a 50% aqueous solution of NaOH over 5 min, followed by the addition of 19 g (0.475 mol) of pulverised NaOH in increments over 45 min and the suspension is stirred for 2.5 h. The suspension is filtered, the residue is washed with 100 ml of toluene and the phases are separated. The organic phase is dried over $MgSO_4$, filtered, and the filtrate is freed from solvent on a rotary evaporator at a bath temperature of 60° C., giving 103.0 g (97% of theory) of colourless glycidyl ether of 4-tert-butylcyclohexanol having the following properties: epoxy value: 4.09 eq/kg (87% of theory); total chlorine content: 1.8%; concentration of hydrolisable chlorine: 270 ppm.

EXAMPLE 12

A 1 liter 3-necked flask equipped with thermometer, stirrer, reflux condenser, and dropping funnel is charged under $N_2$ gas with 50.0 g (0.347 mol) of cyclohexane-1,4-dimethanol and 1.0 g of catalyst H and the reaction mixture is heated to 130° C. With stirring, 163.8 ml (0.69 mol) of epichlorohydrin are added dropwise, and the reaction mixture is thereafter allowed to react for 1 h. After cooling to 40° C., 6.6 g (0.0825 mol) of a 50% aqueous solution of NaOH are added to the solution, followed by the addition of 23.1 g (0.578 mol) of pulverised NaOH in increments over 1 h. The suspension is further stirred, diluted with 155 ml of water and filtered. The organic phase is separated and then dried at 100° C. under vacuum on a rotary evaporator, giving 86.2 g (97% of theory) of glycidyl ether of cyclohexane-1,4-dimethanol as a yellowish liquid having an epoxy value of 6.43 mol/kg (82% of theory) and a total chlorine content of 3.9%.

EXAMPLE 13

A 1 liter 3-necked flask equipped with thermometer, stirrer, reflux condenser, and dropping funnel is charged with 90.0 g (1.0 mol) of 1,4-butanediol and 2 g of a 50% solution of $Fe(H_2O)_y(CF_3SO_3)_2$ in acetonitrile and the mixture is heated to 130° C. With stirring, 185.0 g (2.0 mol) of epichlorohydrin are added dropwise over 1 h and the reaction mixture is allowed to continue to react for 4.5 h. Dehydrohalogenation is then carried out with 80.0 g (2.0 mol) of NaOH as described in Example 12 and the reaction mixture is worked up, giving a low viscosity resin having an epoxy value of 8.20 mol/kg (83% of theory) and a chlorine content of 4.3%.

EXAMPLE 14

In accordance with the general procedure described in Example 12, 108.5 g of 4-tert-butylcyclohexanol and 1.0 g of catalyst H are reacted with 63.8 g of epichlorohydrin under $N_2$ gas, dehydrohalogenation is carded out with 26.4 g of NaOH and the reaction mixture is worked up. The low viscosity resin so obtained has an epoxy value of 3.57 mol/kg (76% of theory) and a total chlorine content of 3.3%.

EXAMPLE 15

40.8 g (0.4 mol) of 1-hexanol and 0.66 g of catalyst A are placed in an autoclave and then 17.6 g (0.4 mol) of ethylene oxide are introduced under pressure. Afterwards the temperature is raised to 100° C. and the reaction mixture is reacted for 12 h at this temperature. Gas chromatographic analysis of the reaction mixture gives the following product distribution (basis percentages):
20.4% of educt,
49.3% of monoadduct,
22.9% of diadduct,
6.0% of triadduct and
0.8% of tetraadduct.

What is claimed is:

1. A process for the for the preparation of an adduct by reacting an alcohol with an epoxy compound in the presence of a catalyst, which comprises reacting an alcohol of formula I

$$A \text{\textemdash} OH]_r \qquad (I)$$

wherein A is an aliphatic, cycloaliphatic or araliphatic radical and r is a number from 1 to 10, with a mono- or diepoxide in the equivalent ratio of 1:20 to 20:1, based on the hydroxyl and epoxy groups, in the presence of a metal complex of formula II as catalyst

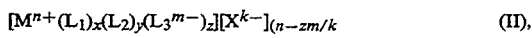

$$[M^{n+}(L_1)_x(L_2)_y(L_3^{m-})_z][X^{k-}]_{(n-zm)/k} \qquad (II),$$

wherein
M is a metal,
$L_1$ is a nitrile, isonitrile, thioether, phosphine, ether, aldehyde, ketone or a $sp^2$-nitrogen-containing compound,
$L_2$ is a water molecule, a nitrile, isonitrile, thioether, phosphine, ether, aldehyde, ketone or a $sp^2$-nitrogen-containing compound, $L_3$ is a phosphine, phosphite, phosphonite, halide, cyanide, alcoholate, thiolate, carboxylate, acetylacetonate, a cyclopentadienyl or sp²-nitrogen-containing compound which is unsubstituted or substituted by one or more than one $C_1$–$C_4$alkyl or tri($C_1$–$C_4$alkyl)silyl group, X is an anion of the formula $BF_4^-$, $PF_6^-$, $AsF_6^-$, $SbF_6^-$, $ClO_4^-$, $IO_4^-$ or $NO_3^-$ or is the sulfonate radical of a perfluorinated alkanesulfonic acid, n is an integer from 1 to 6, m is 0 or an integer from 1 to 6, k is 1 or 2, x is an integer form 1 to 1000, y is 0 or an integer from 1 to 1000, and z is 0 or an integer from 1 to 6.

2. A process according to claim 1, wherein A in formula I is an aliphatic or cycloaliphatic radical.

3. A process according to claim 1, wherein r in formula I is an integer from 1 to 6.

4. A process according to claim 1, wherein the monoepoxide is an epihalohydrin or an alkylene oxide.

5. A process according to claim 1, wherein the monoepoxide is an epihalohydrin.

6. A process according to claim 5, wherein the epihalohydrin is epichlorohydrin, epibromohydrin or β-methylepichlorohydrin and the resultant halohydrin ether is converted by subsequent dehydrohalogenation with a base to give the glycidyl ether of formula III

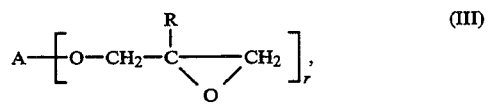

wherein A and r are as defined for formula I in claim 1 and R is a hydrogen atom or methyl.

7. A process according to claim 5, wherein epichlorohydrin is used as epihalohydrin.

8. A process according to claim 5, wherein 0.7 to 2.0 mol of epihalohydrin is used per hydroxy equivalent of the alcohol of formula I.

9. A process according to claim 5, wherein 0.9 to 1.1 mol of epihalohydrin is used per hydroxy equivalent of the alcohol of formula I.

10. A process according to claim 1, which comprises using a compound of formula II wherein M is a metal of main group II, III or IV of the Periodic Table of the Elements, a metal of the transition groups, a lanthanide or actinide, $L_1$ is a nitrile, isonitrile, thioether, phosphine, ether, aldehyde, ketone or a sp²-nitrogen-containing compound, $L_2$ is a water molecule, a nitrile, isonitrile, thioether, phosphine, ether, aldehyde, ketone or a sp²-nitrogen-containing compound, $L_3$ is a phosphine, phosphite, phosponite, halide, cyanide, alcoholate, thiolate, carboxylate, acetylacetonate, a cyclopentadienyl or sp²-nitrogen-containing compound which is unsubstituted or substituted by one or more than one $C_1$–$C_4$alkyl or tri($C_1$–$C_4$alkyl)silyl group, X is an anion of the formula $BF_4^-$, $PF_6^-$, $AsF_6^-$, $SbF_6^-$, $ClO_4^-$, $IO_4^-$ or $NO_3^-$ or is the sulfonate radical of a perfluorinated alkanesulfonic acid, n is an integer from 1 to 3, m is 0 or an integer from 1 to 3, k is 1 or 2, x is an integer from 1 to 10, y is 0 or an integer from 1 to 10, and z is 0 or an integer from 1 to 3.

11. A process according to claim 1, which comprises using a compound of formula II, wherein M is Fe, Sn, Zn, Y or a metal of the lanthanides, $L_1$ is a nitrile, isonitrile, thioether or ether, $L_2$ is a water molecule, a nitrile, isonitrile, thioether or ether, $L_3$ is a phosphine, phosphite, halide or carboxylate, X is an anion of the formula $BF_6^-$, $PF_6^-$ or $ClO_4^-$ or is the trifluoromethanesulfonate radical.

12. A process according to claim 1, wherein the compound of formula II is the metal complex compound $La(CH_3CN)_x(H_2O)_y(CF_3SO_3)_3$ or $La(CH_3CN)_x(H_2O)_y(ClO_4)_3$.

* * * * *